United States Patent [19]

Katz

[11] Patent Number: 5,270,748
[45] Date of Patent: Dec. 14, 1993

[54] HIGH-SPEED EYE TRACKING DEVICE AND METHOD

[75] Inventor: Warren J. Katz, Cambridge, Mass.

[73] Assignee: Mäk Technologies, Inc., Cambridge, Mass.

[21] Appl. No.: 828,477

[22] Filed: Jan. 30, 1992

[51] Int. Cl.⁵ ............................................. A61B 3/14
[52] U.S. Cl. ................................. 351/210; 351/209; 351/221
[58] Field of Search ............... 351/208, 209, 210, 221

[56] References Cited

U.S. PATENT DOCUMENTS

| | | |
|---|---|---|
| 3,462,604 | 8/1969 | Mason. |
| 3,712,716 | 1/1973 | Cornsweet et al. |
| 3,724,932 | 4/1973 | Cornsweet et al. |
| 3,804,496 | 4/1974 | Crane et al. |
| 4,028,725 | 6/1977 | Lewis. |
| 4,109,145 | 8/1978 | Graf. |
| 4,287,410 | 9/1981 | Crane et al. |
| 4,387,974 | 6/1983 | Marshall et al. |
| 4,479,784 | 10/1984 | Mallinson et al. |
| 4,568,159 | 2/1986 | Baldwin. |
| 4,702,575 | 10/1987 | Breglia. |
| 4,720,189 | 1/1988 | Heynen et al. ............... 351/210 |
| 4,815,839 | 3/1989 | Waldorf ............... 351/210 |
| 4,852,988 | 8/1989 | Velez et al. |
| 4,856,891 | 8/1989 | Pflibsen et al. |
| 4,881,807 | 11/1989 | Luce et al. ............... 351/210 |

FOREIGN PATENT DOCUMENTS 63-210613 9/1988 Japan.

OTHER PUBLICATIONS

J. Krauskopf, Measurements of Light Reflected From The Retina, National Research Council, Pub. 1272, pp. 149-170 (1966).

*Primary Examiner*—Bruce Y. Arnold
*Assistant Examiner*—Hung Xuan Dang
*Attorney, Agent, or Firm*—Willian Brinks Olds Hofer Gilson & Lione

[57] ABSTRACT

An eye tracking device that utilizes light detection devices for determining the visual axis and point of regard of a user. The light detection devices are arranged in such a way, such as embedded in a thin film, so as to be curved around the optical axis of the eye. In this way, the light detection devices are always coincident with source-emitted light reflected from the fovea. The curved arrangement of light detection devices are mounted onto a head or facial apparatus, which has a mild reflector on its outside surface to keep external light noise at a minimum. Conversion circuitry, such as a pyramid cascade circuit or a microprocessor circuit, determines the position of the fovea-reflected light and computes the visual axis and point of regard of the user at a very rapid rate.

16 Claims, 11 Drawing Sheets

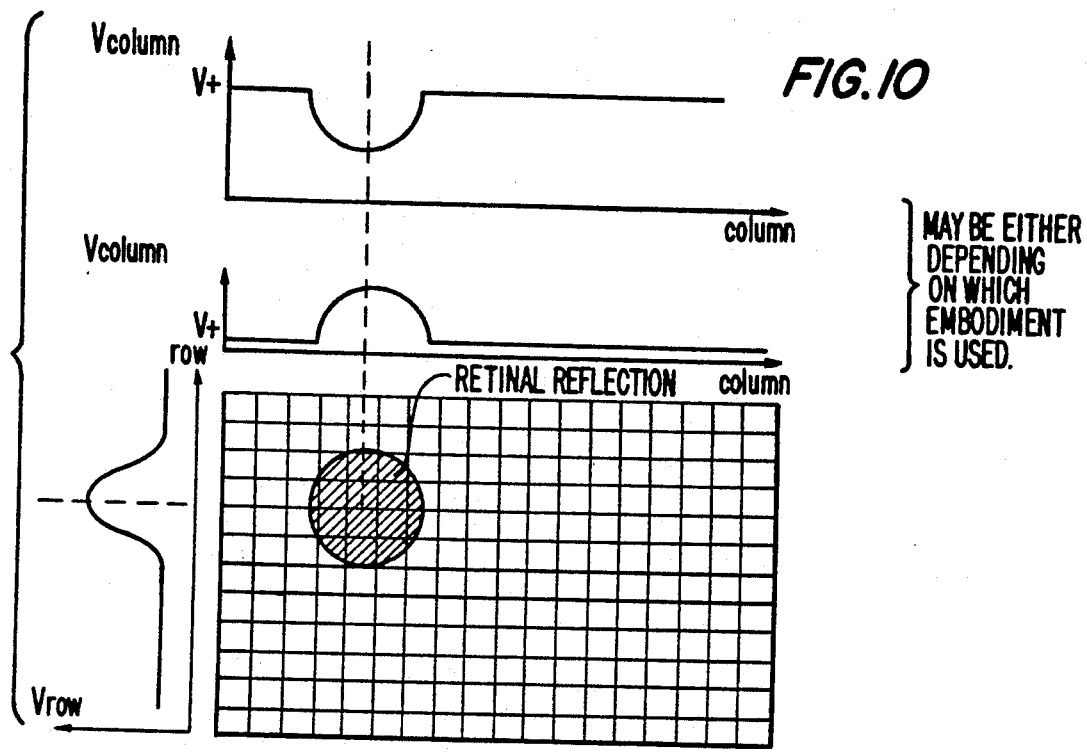

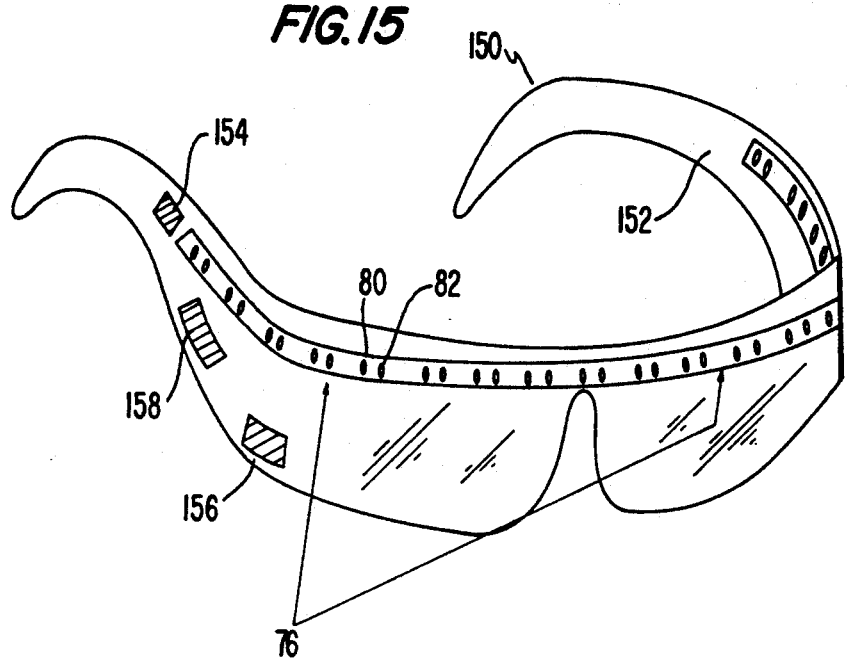
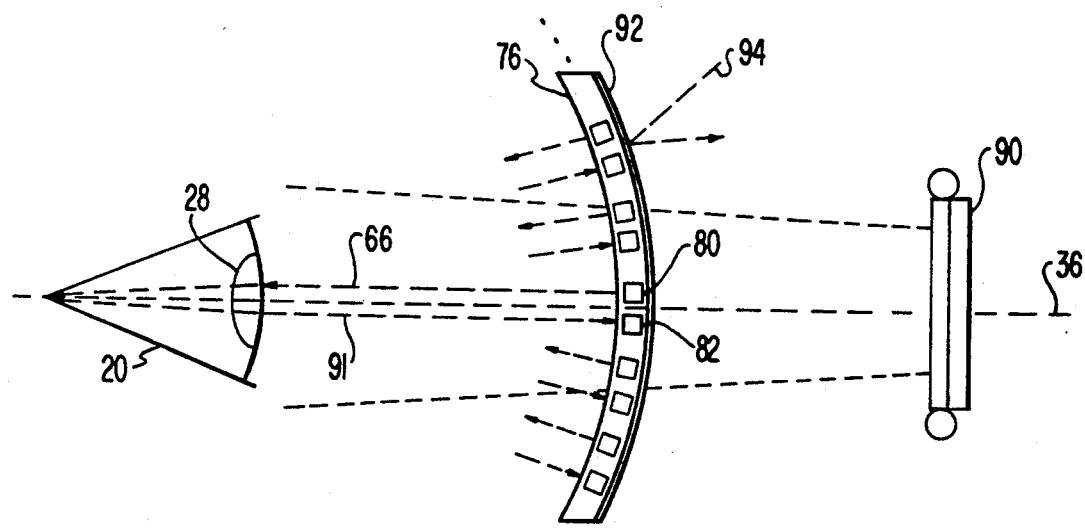

FACE VIEW

SIDE VIEW (EXAGGERATED)

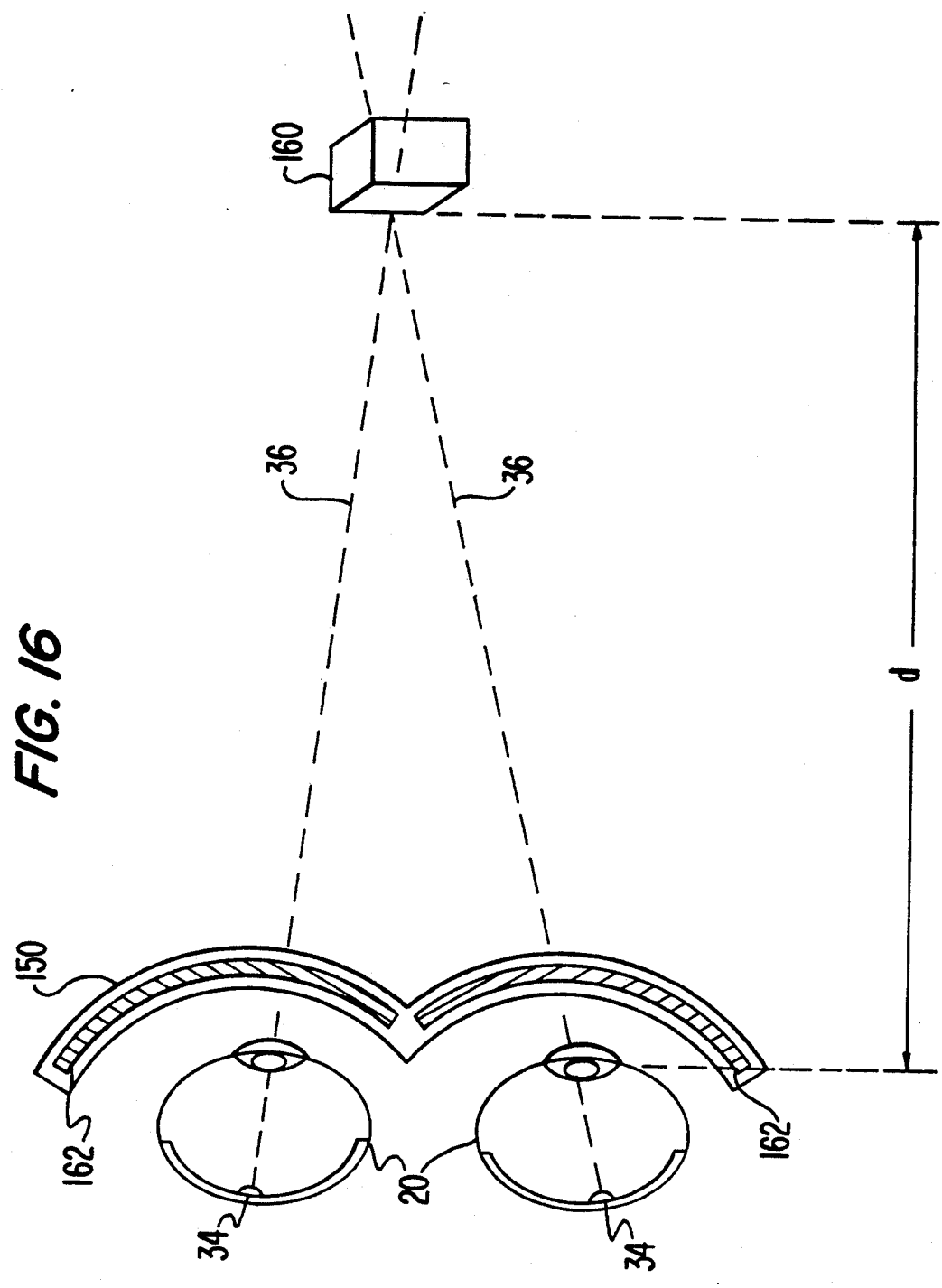

HIGH-SPEED EYE TRACKING DEVICE AND METHOD

BACKGROUND OF THE INVENTION

The present invention relates to an improved eye tracking device used to determine the visual axis and point of regard of a user, and more particularly to an improved eye tracking device which utilizes light detection devices curved around the optical axis of the eye so as to always be coincident with source-emitted light reflected from the fovea, and conversion circuitry for determining the position of the fovea reflected light and computing the visual axis and point of regard at a very rapid rate.

The concept of retinal-reflected light as utilized in the invention is shown in FIGS. 1 and 2. This concept is well known in the art and is discussed only briefly here. A full discourse on the concept is given in J. Krauskopf, *Measurements Of Light Reflected From The Retina*, National Research Council, Pub. 1272, pages 149-170 (1966). FIG. 1 shows the various parts of the eye 20. The outer surface of the eye 20 includes the cornea 22, the sclera 24, the iris 26, and the pupil 28. The inner parts of the eye include the lens 30, the retina 32, and the fovea 34. The position of the fovea 34 generally corresponds with the optical axis 36 of the eye 20. When collimated light is shined directly onto the eye 20 it will be reflected by the various external and internal parts of the eye. The brightest reflection is always that which exits the pupil 28, since light shined onto the pupil 28 passes through it, is focussed onto the retina 32, and is then reflected by the retina 32, and more particularly by the fovea 34. Since the position of the fovea 34 corresponds to the optical axis 36, the visual axis and point of regard can be computed if one can accurately and quickly determine the position of the fovea-reflected light.

FIG. 2 graphically illustrates the concept of eye reflected light and the greater intensity reflection by the fovea 34. The Y axis represents the intensity of light reflected from the eye. 10 The X axis represents the parts of the eye shown in FIG. 1. Points 1 and 2 on the graph correspond to light reflected from the sclera 24. Points 3 and 5 correspond to light reflected from the iris 26. Point 4 corresponds to the brightest reflected light, that from the pupil 28 (which is from the fovea 34), as expected.

The frequency of light used for reflection off the eye and retina plays an important role in determining the visual axis and point of regard. As is known in the art, only light within the visible spectrum range is capable of being reflected by the eye and retina. The use of infrared light, then, is unacceptable, since the eye absorbs all infrared light and therefore no reflection will occur. On the other hand, plainly visible light is not acceptable either, since shining visible light into a user's eye will of course result in a blinding effect, and thus no useful point of regard data can be obtained. Therefore, it is necessary to use light which falls within the visible spectrum but will still be transparent to the eye's (specifically, the fovea's) sensitivity. Near infrared light is the type most suitable for these purposes, since it falls within the upper limit of the visible spectrum but will not appear visible to a user, since it is outside foveal sensitivity. FIG. 3 graphically depicts this concept. The visible spectrum generally falls between light wavelengths of 380 to 740 nanometers (nm), and the infrared light range starts at about 743 nm. Peak foveal sensitivity is around 555 nm. Light most suitable for foveal reflection is the near infrared light on the upper end of the visible spectrum, about 675 to 740 nm. Preferably, near infrared light of 700 to 740 nm is used, and most preferably near infrared light from 720 to 740 nm.

Prior art eye tracking devices have relied on various eye characteristic concepts to determine the eye's position. FIGS. 4A and 4B illustrate two of these concepts. FIG. 4A is the basis for corneal reflex (oculometer) eye tracking devices. An enlargement of the eye 20 is shown. The optical axis 36 is aligned with the center of the pupil. Light 40 from a source within the oculometer (not shown) is reflected by the cornea 22. A video camera (not shown) looking at the eye 20 finds the brightest spot on the eye, which is the reflection from the cornea 22, and also finds the darkest spot on the eye 20, which is the pupil 28. A video processing computer (not shown) computes the location of the center of the pupil 28 from the picture provided by the video camera. The displacement of the corneal reflection from the center or rne pupil is K sin $\theta$, which is proportional to the angular direction, $\theta$, of the eye 20. This displacement is independent of the position of the eye 20 in its socket (not shown). By determining the displacement of the corneal reflection from the center of the pupil, an approximation of the point of regard may be computed.

FIG. 4B represents a concept known as Purkinje images, which is also utilized in prior art eye detection devices. As light 40 passes through the eye, reflections occur at every interface in which there is a change in dielectric constant. There are four surfaces where these reflections occur: the front of the cornea 22, the back of the cornea 22, the front of the lens 30, and the back of the lens 30. These reflections correspond to the four Purkinje images, respectively. The fourth Purkinje image is almost the same size and is formed in almost the same plane as the first Purkinje image, although it is over 100 times less intense. If the eye rotates, these two images change their separation in space because the surfaces that form the first and fourth Purkinje images have centers of curvature that lie at different distances from the center of rotation of the eye. The physical separation between the first and fourth Purkinje images in space is a measure of the angular rotation of the eye in the direction of the rotation. By determining the distance of the separation of the first and fourth Purkinje images, an approximation of the point of regard can be calculated. Again, this requires the use of a video camera to find the Purkinje images and a video processing computer to compute the location of the Purkinje images A typical prior art eye tracker that utilizes the Purkinje image concept is disclosed in Crane et. al., U.S Pat. No. 4,287,410.

While both of the concepts described in FIGS. 4A and 4B above have improved the field of eye detection devices, there are disadvantages to their use. Both methods require a video camera to be mounted in a fixed position relative to the eye. This usually entails use of a cumbersome helmet mounted device. Both methods also require expensive and slow video processing computer hardware to process the image from the camera. Additionally, the range of eye motion that these methods can detect is very small. Large excursions of the eye within the socket result in the reflections being removed from the camera eye.

A typical example of another type of prior art eye detector is shown in Japan Pat. No. 63-210613. which discloses a glance direction detector whereby a matrix of light emitting diodes emit infrared light that is reflected by a mirror so as to reflect off the retina. The retina-reflected light is in turn reflected off another mirror and is detected by a light receiving body such that the glance direction of the eye is detected. Although providing improvements over previous prior art eye detectors, the disadvantages of such a system are at least three-fold: the use of reflecting mirrors requires a great amount of precise calibration in order for the device to function properly; the mirrors must be very large in order to reflect wide angle changes in the position of the eye, resulting in the mirrors taking up an unacceptable amount of surface area; and perhaps the greatest disadvantage is that the use of only one light receiving body on a flat surface results in non-linear eye location information being outputted, depending on the extremity of the eye's position. This is because the distance the reflected light travels from the eye to the light receiving body will vary as the eye moves in the socket. The ultimate result is that only an approximation of the actual eye position is given, which is unacceptable to those requiring accurate eye position data, or alternatively computer mapping will be required, which is prohibitively costly and time consuming.

Other prior art devices are of the type epitomized by Baldwin, U.S. Pat. No. 4,568,159. Baldwin shows a head and eye position indicator that utilizes an infrared light source reflected from the cornea of the eye to yield eye position, as well as additional coded infrared sources which are reflected and detected to determine head position. Baldwin uses an array of infrared emitters dispersed around a spherical dome upon which the visual presentation is displayed. The infrared emitters are coded such that each can be identified by its location on the dome. The reflected infrared light is transmitted via a fiber optic means to a charge coupled diode array which provides a high speed conversion into electrical impulses indicative of the relative positions of the sources within the field of view of the user, so that head and eye position may be computed. Although the invention in Baldwin provides advantages in the field of flight simulation by disclosing a head tracker and eye tracker used in tandem, it does not provide any innovation in the field of eye tracking devices alone, and thus the same problem with respect to non-linear eye position information being outputted occurs, as described above.

In addition, visual systems that employ the use of eye tracking devices are exemplified by Mallinson et. al,. U.S. Pat. No. 4,479,784, which discloses a visual system for providing high detail, high resolution imagery anywhere a user is looking throughout a wide field of view. The Mallinson system detects changes in the instantaneous position of the eye using a helmetmounted oculometer system to provide a foveal view, or high detail image, at the next lookpoint. Thus, while Mallinson discloses an improved visual system, the use of a prior art eye detection device will limit the effectiveness of the system due to non-linear eye position information being outputted, as has heretofore been described.

The prior art also discloses circuitry for use in eye tracking devices. For example, Marshall et. al,. U.S. Pat. No. 4,387,974 discloses a circuit for calculating the position of the cornea using a dual axis infrared light detector responsive to pulsed infrared light reflected from the corneal area of the eye, such that the X and Y coordinate positions of the cornea are determined. Although this type of circuit improves over the prior art by providing enhanced position measurement accuracy and response time, there still exists a need for improved position accuracy and a faster response time than currently disclosed in the prior art.

While the prior art provides important advantages, there still exists the need for a relatively lightweight, highly accurate eye tracking device that computes the visual axis and point of regard at rates faster than that known in the prior art. Thus, what is disclosed is an improved eye tracking device, which utilizes a plurality of light emission sources and a plurality of light detection devices mounted in such a way on a head apparel device so as to always be co-incident with the axis of the eye. In this manner, the need for mirror calibration is eliminated. Another aspect of this invention that improves over the prior art is the use of conversion circuitry, such as a pyramid cascade circuit or a microprocessor and digital multiplexor, that computes the visual axis and point of regard at speeds faster than any previously disclosed eye tracker. A further advantage occurs by embedding the light emission devices and the light detection devices into a thin film of transparent polymer. By curving the thin film of transparent polymer to match the curvature of the eye, and mounting the curved thin film onto the inside surface of a head apparel device so that it extends around the inside surface and corresponds to the visual field of view, the problem of non-linear eye position information is solved. A still further advantage is the use of a mild reflector on the outside surface of the head apparel device in order to keep the amount of external light that impinges on the detection devices (i.e., light noise) at a minimum. Practical advantages upon implementation will also be apparent. The entire device may be embedded in the curved thin film, resulting in a one-piece, sturdy, solid-state eye tracker. Also, the elimination of video cameras and video processing computers results in relatively low implementation costs. All of these advantages result in highly accurate eye position information being outputted at extremely rapid rates.

SUMMARY OF THE INVENTION

According to this invention, a plurality of light emission devices and a plurality of light detection devices are embedded in a thin layer of transparent film, the transparent film being curved in such a way that it matches the curvature of the eye. An example of thin film that may be utilized in the invention is a transparent polymer. It is intended that the curved transparent film be mounted on the inside surface of a head or facial apparel device, such as a helmet, visor, or goggle apparatus, so that the light emission devices and the light detection devices are always co-incident with the optical axis of the eye, regardless of the position of the eye in its socket. In order to accomplish this, it is intended that the curved transparent thin film, and the embedded light detection and light emission devices, extend around the inside surface of the apparel device, corresponding to all the possible positions of the optical axis of the eye. In this way, linearity of results is assured.

The plurality of light emission devices emit light for reflection off the parts of the eye. Specifically, it is intended that the emitted light pass through the pupil for reflection off the retina, such that the brightest reflection is off the fovea. This reflected light is then detected by the light detection devices. The apparel device is equipped with a mild reflector on its outside surface in order to keep the amount of external light that impinges on the light detection devices (i.e., light noise) at a minimum. The light reflected from the eye and detected by the light detection devices is converted into digital values by conversion circuitry (discussed in detail below), whereby the highest value corresponds to the brightest reflected light, i.e., the light reflected from the fovea. The conversion circuitry reads the digital values and computes the visual axis and point of regard at speeds faster than any of the eye tracking devices or eye tracking circuitry currently known in the art.

In another embodiment of the invention, the disclosed invention is combined with other technology to make a wireless head-eye tracker apparatus, which utilizes the disclosed invention in unison with one of the conversion circuits disclosed. A wireless head tracking device is built into the frame of the apparatus, as is a wireless local area network device. The local area network device transmits the eye tracking information and the head tracking information to a remote computing station, where the information can be utilized. Thus, a lightweight, one-piece mobile head and eye tracking device is disclosed.

In still another embodiment of the invention, the transparent polymer is curved so as to be exactly calibrated to a specific user. In this embodiment, the precise curvature of a particular user's eye is measured, and the transparent thin film (or polymer) is then curved to exactly match the measured eye. In this way, even the most minute discrepancies of a particular user's eye will be accounted for, yielding extremely accurate eye position information.

In still yet another embodiment of the invention, two eye tracking devices, one for each eye, are used in unison to determine which object in three dimensional space the user is focussing on. When a person looks at an object, each eye independently places the object into foveal view, producing a fused image of the object for the brain. Because the invention is lightweight, low cost, and extremely accurate, an eye tracking device may be placed on each eye, so as to determine each eye's optical axis. The intersection of the two optical axes is the point in three dimensional space the user is looking at. By simple geometry, the distance between the object in space and the user may be determined. Thus, this dual eye tracking device may be used to identify the position of three dimensional objects in space, for applications such as CAD/CAM or other computer applications requiring an indication of a three dimensional point in space by the user.

In a preferred embodiment of the invention, the light emission devices are a matrix of light emitting diodes, and the light detection devices are a corresponding matrix of photodetectors, whereby the sensitivity of the photodetectors are tuned to the emission frequency of the light emitting diodes.

In another preferred embodiment of the invention, the conversion circuitry used for computing the visual axis and point of regard is a pyramid cascade circuit. This utilizes a plurality of read only memory words containing the hard coded address for each row and column of the light detecting devices or the transparent optical layer, a plurality of analog to digital converters for converting the voltage output of each row and column to a numerical value, and a plurality of comparators between each pair of the rows and columns for comparing the numerical values and selecting the larger of the two. The larger of the numerical values and its corresponding address is then passed up to the next level of comparators, where the process is repeated until the address with the greatest numerical value is determined. This address corresponds to the point of incidence of the fovea-reflected light, and thus the visual axis and point of regard is determined. The pyramid cascade circuit determines the visual axis at speeds faster than any eye tracker currently known.

Alternate embodiments of the invention described are possible. In one alternate embodiment, there is disclosed a peripheral light source and a transparent optical layer overlaid with transparent resistive strips in a row and column configuration. It is intended that the transparent resistive strips change resistance according to the amount of light impinging upon them. The optical layer and resistive strips are given a reflective coating on their outer surface that is specifically reflective to the peripheral light source frequency. As in the previous embodiment, the optical layer and resistive strips are mounted on the inside surface of a head or facial apparel device and curved in such a way so as to match the curvature of the eye. Again, it is intended that the optical layer and resistive strips extend around the inside surface of the apparel device, corresponding to the optical axis of the eye. It is also intended that the apparel device be equipped with a mild reflector on its outside surface in order to keep the amount of external light that impinges on the resistive strips (i.e., light noise) at a minimum.

The peripheral light source shines light evenly into the transparent optical layer. Due to the reflective coating on the outside surface of the transparent optical layer and the transparent resistive strips, the emitted light is "bounced" around the transparent optical layer until it issues from the holes or spaces between the transparent resistive strips. This light then reflects off the parts of the eye and returns to the uncoated side of the transparent resistive strips. This light impinges on the strips and causes their resistance to change, such that the location of the fovea-reflected light on the transparent optical layer can be determined. Using conversion circuitry identical to the type in the previous embodiment, the visual axis and point of regard can be computed.

In another alternate embodiment of the invention, the conversion circuitry used for computing the visual axis and point of regard contains a microprocessor, a plurality of analog to digital converters for converting the voltage output of each row and column of the light detection devices or the transparent optical layer to a numerical value, and a digital multiplexor for selecting the line given by the corresponding address of each numerical value. The microprocessor is programmed in such a way that it sorts through all of the rows and columns, determines which has the highest numerical value, and outputs the address of the row and column with the highest value. This address corresponds to the point of incidence of the fovea-reflected light, and thus the visual axis and point of regard is determined. The microprocessor, while not as fast as the pyramid cascade circuit, still determines the visual axis at speeds faster than any eye tracker currently known.

As pointed out in greater detail below, the eye tracking device disclosed in the present invention provides important advantages over heretofore known eye trackers. For example, the ability to curve the transparent polymer or the transparent optical layer results in the light detecting devices always being co-incident with the optical axis of the eye, so as to yield highly accurate, linear eye position results. Another important advantage of this invention is the use of conversion circuitry to determine the location of fovea-reflected light, such as a pyramid cascade circuit or a microprocessor circuit, that computes the visual axis and point of regard at speeds faster than any previously disclosed eye tracker. Yet another advantage is the use of a mild reflector on the outside surface of the transparent polymer or transparent optical layer in order to keep the amount of external light that impinges on the detection devices (i.e., light noise) at a minimum, thus increasing the accuracy of the eye position results. Implementing the devices in thin film results in a lightweight, mobile one-piece eye tracker that eliminates the need for cumbersome mirrors and video cameras.

The invention itself, together with further objects and attendant advantages, will be best understood by reference to the following detailed description, taken in conjunction with the accompanying drawings.

BRIEF DESCRIPTION OF THE DRAWINGS

FIG. 9 is a typical circuit of a preferred embodiment of the invention showing a matrix of light emitting diodes and a corresponding matrix of phototransistors for determining the reflection from the fovea;

FIG. 10 is a graph of the voltage output of the light detection devices or the resistive strips in the optical layer as a function of retinal reflection;

FIG. 11 is a depiction of a preferred embodiment of the invention, using a matrix of light emitting diodes and a corresponding matrix of photodetectors;

FIG. 15 illustrates one embodiment of the invention, a wireless head-eye tracker apparatus; and FIG. 16 illustrates another embodiment of the invention, a dual eye tracking device for determining three dimensional points in space.

DETAILED DESCRIPTION

Figure 5:
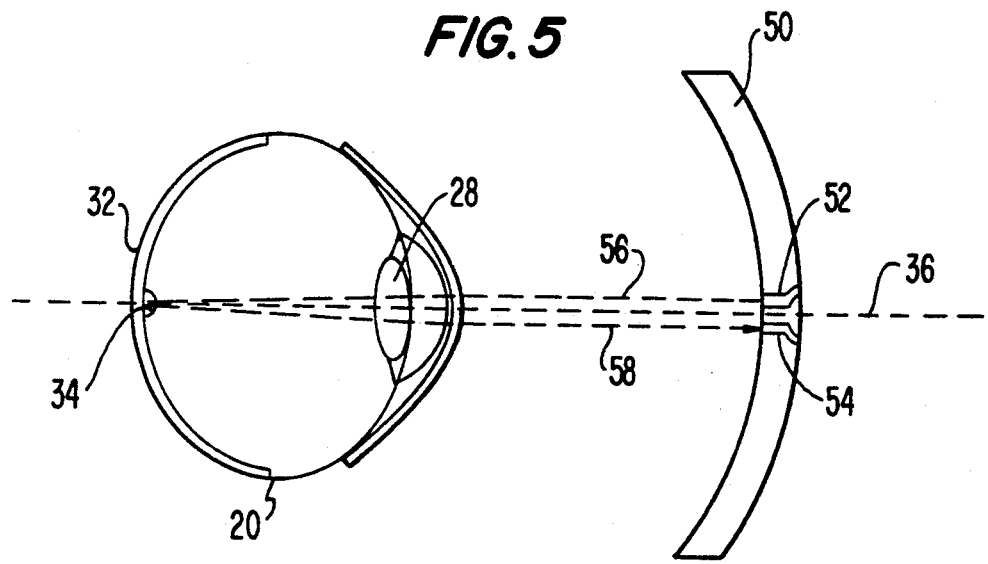
FIG. 5 is a depiction of the concept of the invention.

Turning now to the drawings, the concept behind the present invention is shown in FIG. 5. A surface means 50 is curved to match the curvature of the eye 20. It is intended that the surface means 50 be any type of material conducive to bending or curving, such as glass, lexan, or polymer. Mounted on the surface means 50 is a light emission means 52 and a light detection means 54. The light emission means 52 may be any type of source capable of emitting a diffuse wave of near infrared collimated light, the only restriction being it must be small enough such that the user cannot see it, i.e., it will appear transparent such that the user is able to look through it. A source suitable for these requirements is a light emitting diode of the type manufactured by Panasonic Corp. The light detection means 54 may be any device capable of detecting diffuse collimated near infrared light waves, such as a photodetector or phototransistor. A photodetector suitable for these requirements is manufactured by Kopin Corp.

The light emission means 52 emits light 56 in the direction of the eye 20. The emitted light 56 that corresponds to the path of the optical axis 36 passes through the pupil 28 and reaches the retina 32. The emitted light 56 that contacts the fovea 34 is reflected back through the pupil 28. This fovea-reflected light 58 is detected by the light detection means 54. As will be more fully described, the visual axis and point of regard may be computed from the fovea-reflected light 58 detected by the light detection means 54.

Figure 6:
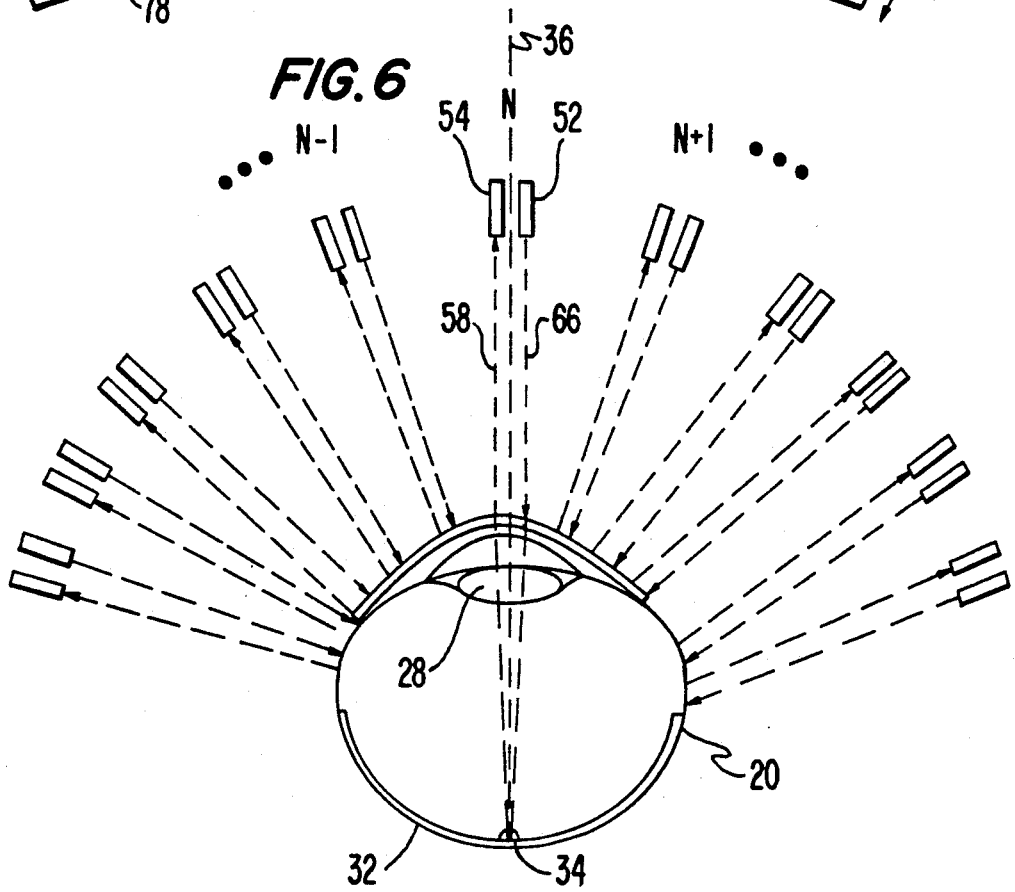
FIG. 6 shows a matrix of light emission devices and a corresponding matrix of light detection devices extending around the optical axis of the eye, so as to always be co-incident with the optical axis.

One of the embodiments of the current invention is depicted in FIG. 6. A plurality of light emission means 52 and a plurality of light detection means 54 are positioned around the eye 20 in such a way that they correspond to the curvature of the eye 20. The plurality of light emission means 52 emit near infrared collimated light 66 in the direction of the eye 20. The near infrared collimated light 66 emitted from the light emission means 52 that corresponds to the position of the optical axis 36 passes through the pupil 28 and reaches the retina 32. The near infrared collimated light 66 is focussed by the pupil 28 onto the fovea 34 and is reflected back through the pupil 28. This fovea-reflected light 58 is detected by the light detection means 54 that corresponds to the position of the optical axis 36. Since the fovea-reflected light 58 is always the brightest light reflected from the eye 20, as discussed above, the visual axis and point of regard may be computed by determining which light detection means 54 has detected the fovea-reflected light 58.

FIG. 6 also shows one of the important advantages of the current invention. As stated previously, the plurality of light emission means 52 and the plurality of light detection means 54 are positioned so as to match the curvature of the eye 20. It necessarily follows that the distance travelled by the fovea-reflected light 58 to reach the light detection means 54 that corresponds in position to the optical axis 36 remains constant, regardless of a change in angular position of the eye 20 in the socket (not shown). Thus, the problem of reflection distances from the eye to the light detection means varying as the eye changes position (i.e., non-linearity), which is present in the prior art, is eliminated.

Figure 1:
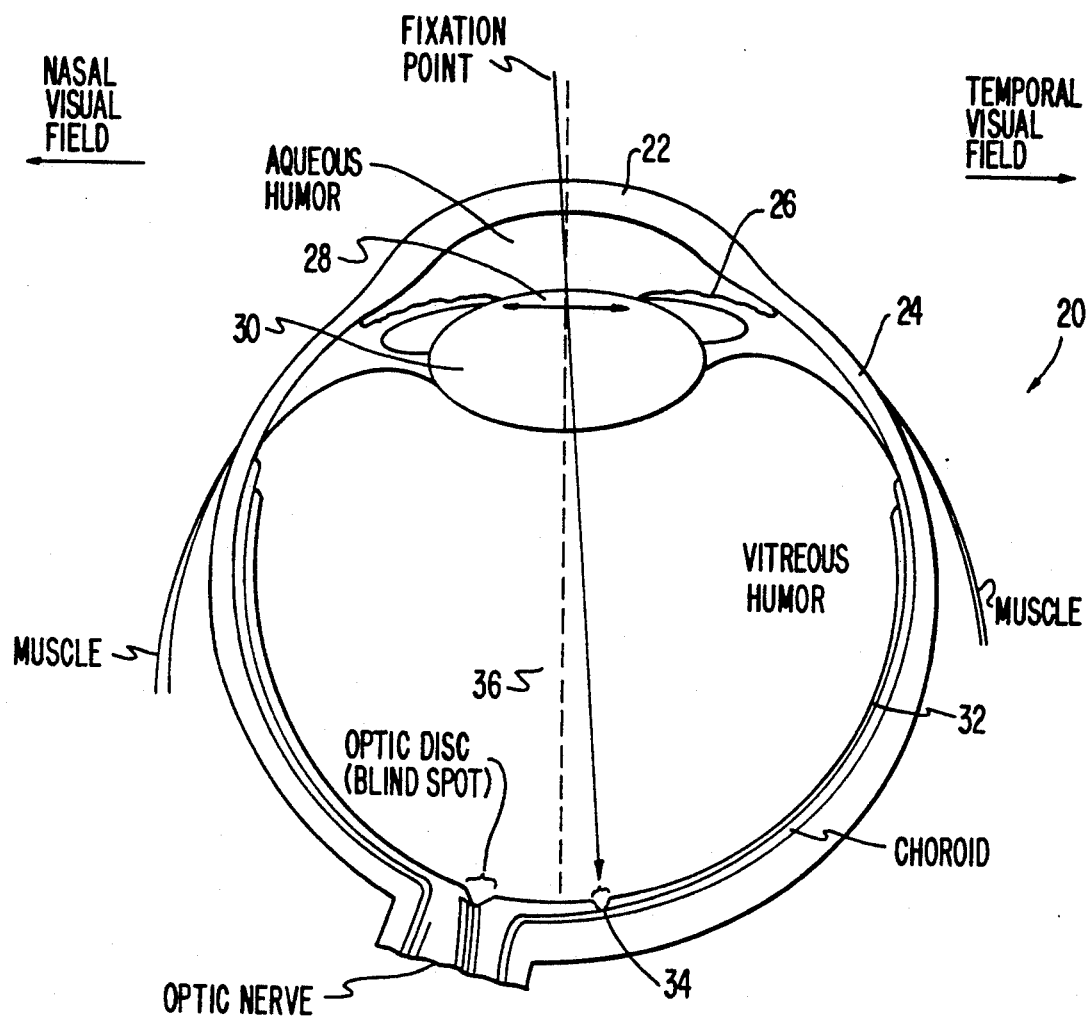
FIG. 1 shows the anatomy of the human eye.
Figure 3:
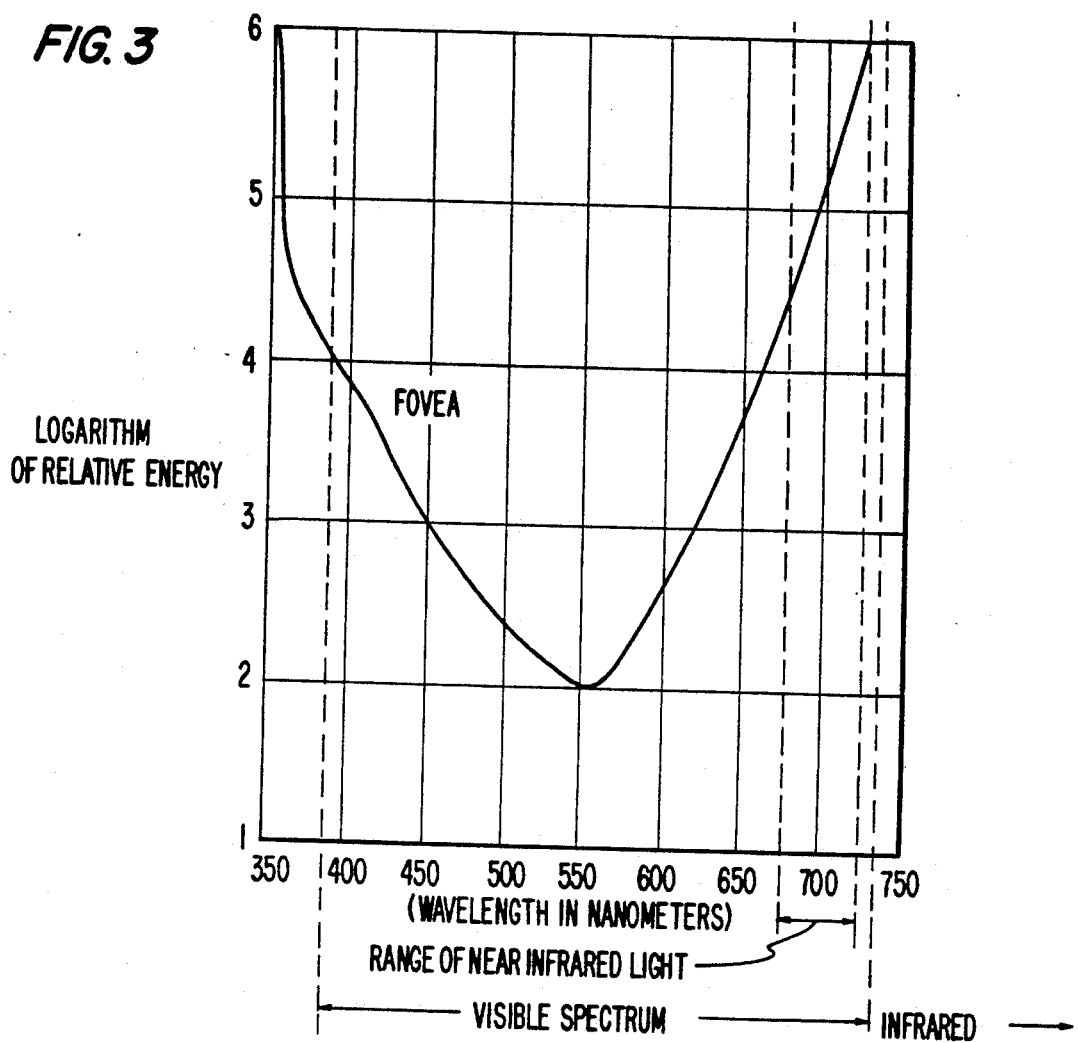
FIG. 3 is a graph of the wavelength of light and the range of near infrared light utilized in the invention.
Figure 2:
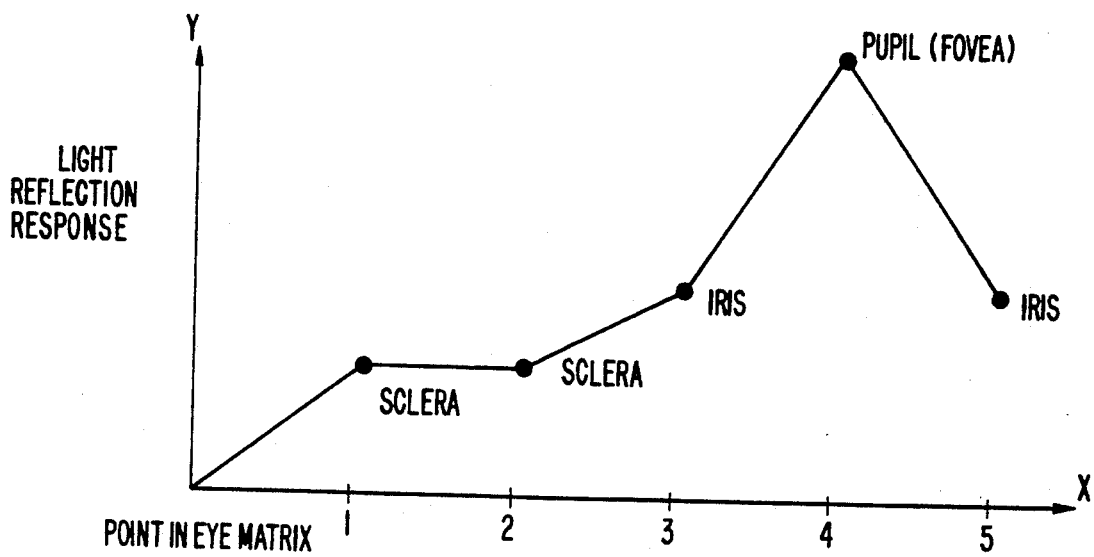
FIG. 2 is a graph of the response of collimated light reflected from different parts of the eye.
Figure 4A:
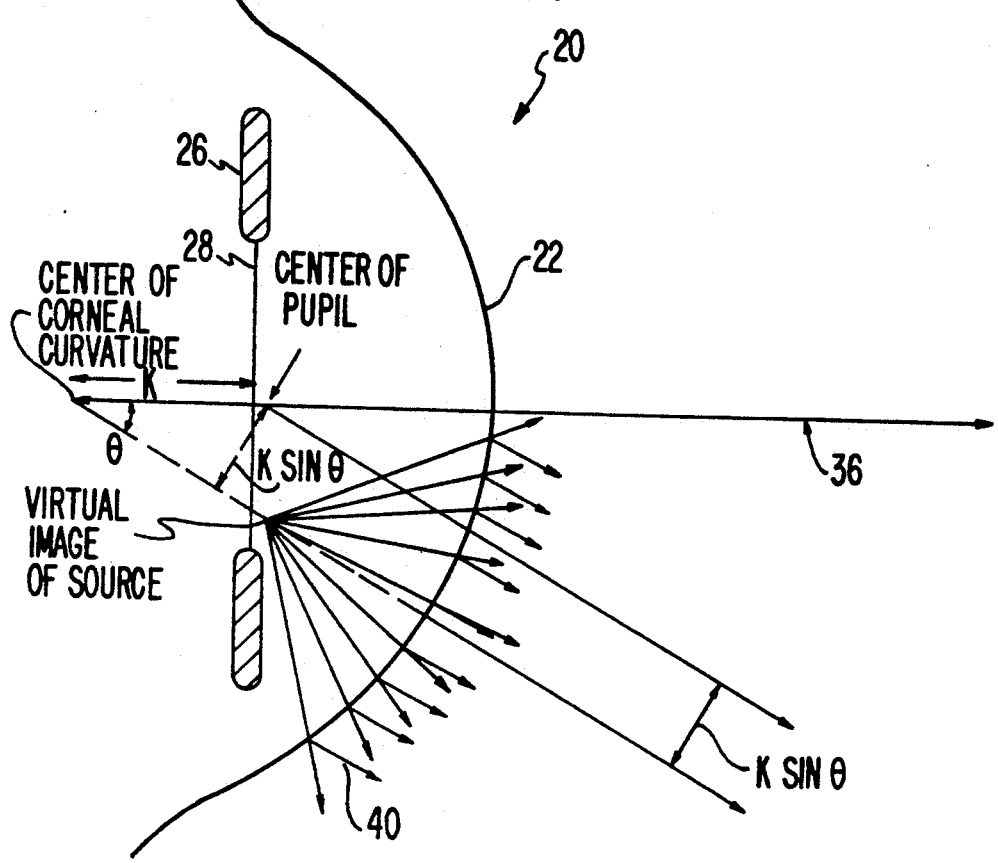
FIGS. 4A and 4B show eye characteristic concepts utilized in prior art eye trackers.
Figure 4B:
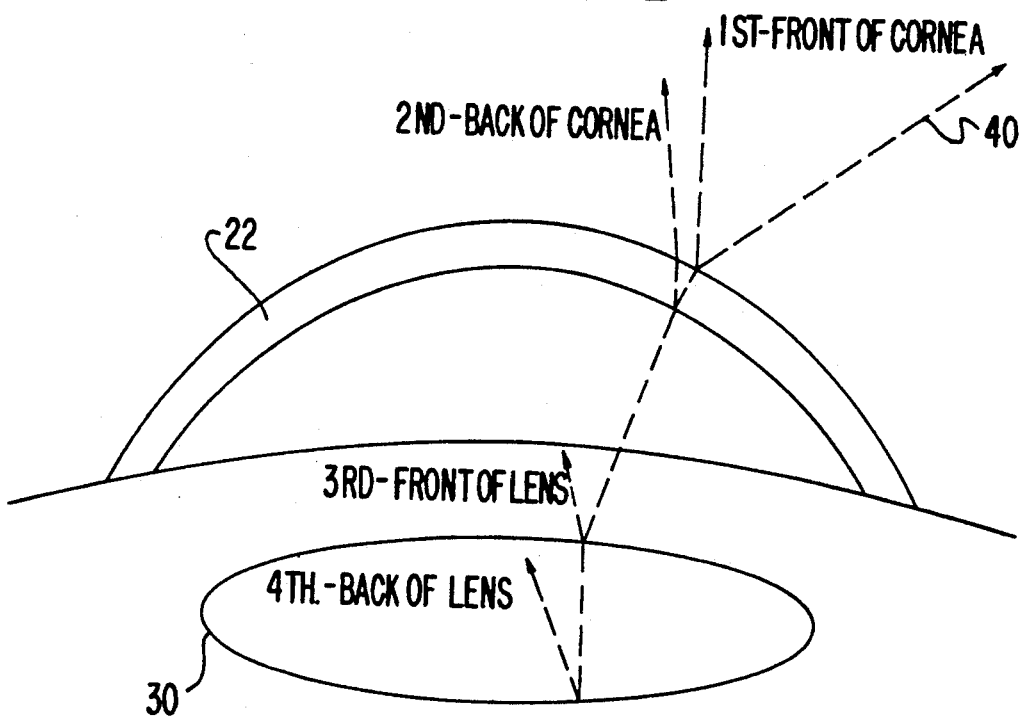
Figure 7A:
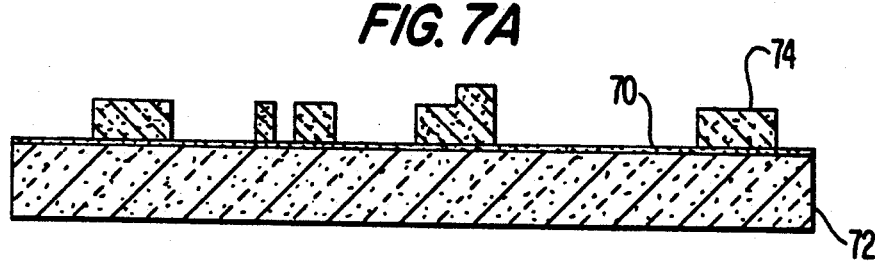
FIGS. 7A, 7B, and 7C are sectional views of the thin film technology utilized in the invention.
Figure 7B:
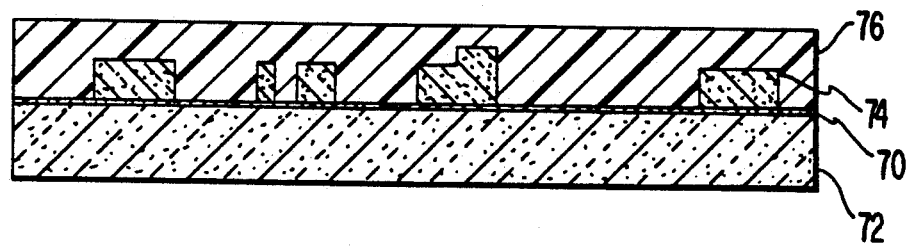
Figure 7C:
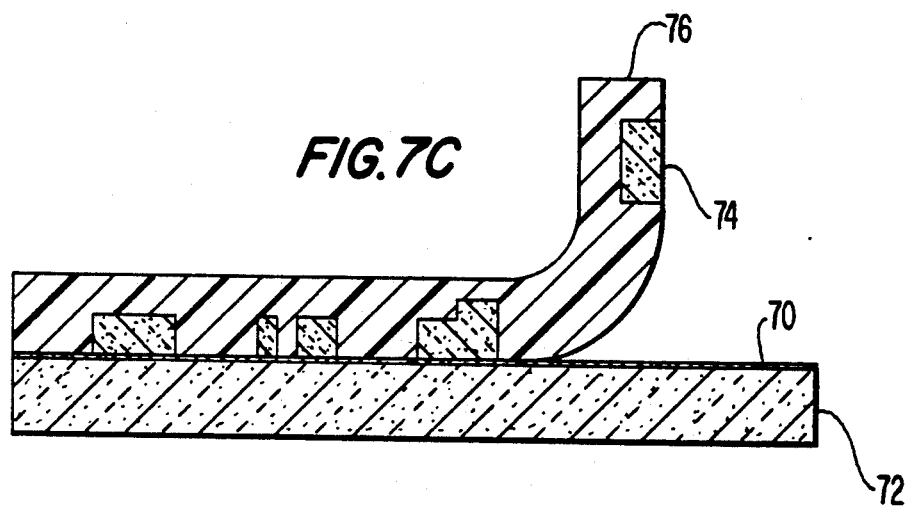

FIGS. 7A, 7B, and 7C show generally the thin film technology utilized in one of the preferred embodiments of the invention. For purposes of illustration only, FIG. 7A depicts an oxide layer 70 applied over a silicon wafer 72. A plurality of semiconductor devices 74 are mounted onto the oxide layer 70 and the silicon wafer 72, as is well-known in the integrated circuit and semiconductor fields. In the next step, shown in FIG. 7B, a layer of a transparent thin film (or polymer) 76 is applied over the semiconductor devices 74. As shown in FIG. 7C, the layer of transparent polymer 76 can then be removed from the silicon wafer 72 by dissolving the oxide layer 70, so that the semiconductor devices 74 remain embedded in the transparent polymer 76. Thin film technology suitable to this invention is manufactured by Kopin Corp.

Figure 8A:
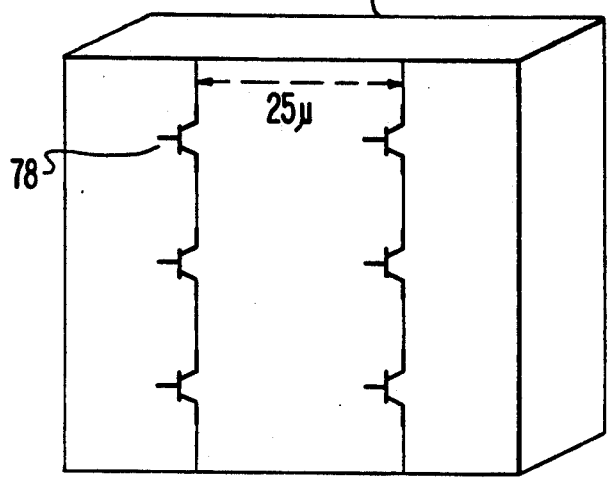
FIGS. 8A and 8B show the relative thickness of the thin film used in the invention and its ability to be curved so as to match the curvature of the eye.
Figure 8B:
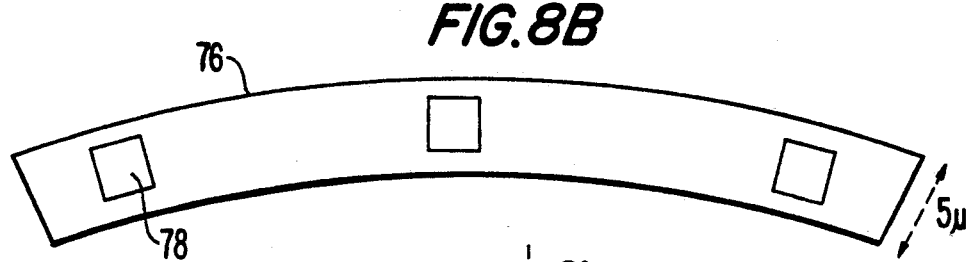

Turning now to FIGS. 8A and 8B, the advantages of using thin film technology in the present invention becomes evident In order to accurately determine the precise position of the eye, the plurality of light emission means 52 and the plurality of light detection means 54 must be placed sufficiently close together to account for even the most minute movements of the eye. Using phototransistors as an example in FIG. 8A, the phototransistors 78 are embedded in the transparent polymer 25 microns apart. This allows for even the slightest eye movement to be detected. Further, FIG. 8B depicts the total thickness of the transparent polymer 76 to be only 5 microns. Thus, the invention is thin enough and light enough to be attached to any type of head or facial apparel, such as helmets, goggles, glasses, or the like. Additionally, FIG. 8B shows the flexibility of the transparent polymer 76, so that it may be curved to match the curvature of the eye.

A circuit of the type used in a preferred embodiment of the invention is shown in FIG. 9. In this embodiment, the light emission means are light emitting diodes, and the light detection means are photodetectors. As discussed previously, a light emitting diode suitable for use in this invention is manufactured by Panasonic Corp., and a photodetector suitable for use in this invention is manufactured by Kopin Corp. The light emitting diodes 80 are embedded into the transparent polymer 76 in a matrix configuration, and the photodetectors 82 are also embedded into the transparent polymer 76 in a matrix configuration, such that for every light emitting diode 80, there is at least one corresponding photodetector 82. It is intended that the photodetector 82 be placed at a sufficient distance from the light emitting diode 80 such that the photodetector 82 is able to acquire the reflected light emitted by the light emitting diode 80, but still maintains the transparency of the device to the user. As an illustrative example only, the light emitting diode 80 may be separated from the photodetector 82 in FIG. 9 by a distance (d) roughly equivalent to three light emitting diode diameters.

The light emitting diodes 80 emit near infrared collimated light of a specific frequency directly out of the plane of the page, towards the eye (not shown). The sensitivity of the photodetectors 82 are tuned to the emission frequency of the light emitting diodes 80. Reflected light from the retina, and specifically the fovea, along the optical axis is detected by the photodetectors 82, causing an increase in $V_{BE}$ (the voltage across the base 84 and emitter 86 of the photodetector 82). When $V_{BE}$ exceeds the conduction threshold (approximately 0.6 volts), current begins to flow from the collector 88 to the emitter 86 of the photodetector 82. Since all the collectors 88 in the vertical column of photodetectors 82 are connected to the same source (V+), and all the emitters 86 are connected in a horizontal row to the same sink (V−), it follows that:

$$i_{column} = \Sigma i_{c(n)},$$

which simply states that the total current in any column of photodetectors 82 is the sum of the currents running through the collectors of each of the photodetectors 82, where n equals the number of photodetectors. By using a resistor $R_c$ as shown in FIG. 9, $V_{column}$ can be determined using Ohm's law:

$$i_{column} = \frac{V+ - V_{column}}{R_c}$$

or $$V_{column} = V+ - i_{column}R_c$$

Thus, the net result is that the column of photodetectors 82 which has the highest intensity reflected light impinging upon it will have the lowest $V_{column}$. The same situation conversely exists for the horizontal rows of photodetectors 82. Since all the emitters 88 in the row are wired together:

$$i_{row} = \Sigma i_{e(n)},$$

which simply states that the total current in any row of photodetectors 82 is the sum of the currents running through the emitters of each of the photodetectors 82, where n equals the number of photodetectors. Using resistor $R_r$ as shown in FIG. 9 and Ohm's law, $V_{row}$ can be determined:

$$i_{row} = \frac{V_{row} - V-}{R_r}$$

or $$V_{row} = i_{row}R_r + V-$$

Here, the net result is that the row of photodetectors 82 which has the highest intensity reflected light impinging upon it will have the highest $V_{row}$.

FIG. 10 graphically depicts $V_{row}$ and $V_{column}$ as a function of the location of the fovea reflection in the photodetector matrix. The row and column of the photodetector matrix that have the highest intensity reflected light impinging upon them (i.e., the light reflected from the retina, and more specifically, the fovea) will output the highest (or lowest) voltage values. From this, the visual axis and point of regard may be computed. The two methods of determining the highest (or lowest) voltage values are fully described below.

FIG. 11 shows the implementation of the preferred embodiment discussed above. A matrix of light emitting diodes 80 and a corresponding matrix of photodetectors 82 are embedded in a thin film of transparent polymer 76. The transparent polymer 76 is curved in such a way so as to match the curvature of the eye 20. The transparent polymer 76 is mounted on a head apparel means (not shown) and extended around the head apparel means so as to be aligned with the optical axis 36 of the eye 20. Thus, there is always a light emitting diode 80 and a corresponding photodetector 82 that is coincident with the optical axis 36 of the eye 20, regardless of the position of the eye 20 in the socket (not shown). As discussed previously, this configuration eliminates the possibility of non-linear eye position data being outputted. It is contemplated that the head apparel means be any type of head or facial apparel, such as helmets, goggles, glasses, or the like, and is not limited to those discussed here.

As shown in FIG. 11, the eye 20 focuses on a remote object, such as a liquid crystal display 90. The light emitting diodes 80 emit near infrared collimated light 66 in the direction of the eye 20. The frequency of the near infrared collimated light 66 is in the wavelength range of 675 to 740 nm, preferably 700 to 740 nm, and most preferably 720 to 740 nm. The sensitivity of the photodetectors 82 are tuned to the emission frequency of the light emitting diodes 80. The near infrared collimated light 66 contacts various parts of the eye 20, such as the pupil 28, and is reflected back towards the photodetectors 82. The highest intensity reflected light 91 is that from the fovea (not shown), as previously discussed. As the eye 20 follows events on the liquid crystal display 90, the optical axis 36 constantly changes. However, there is always at least one photodetector 82 in the photodetector matrix that is coincident with the optical axis 36. Thus, the exact position of the eye 20, i.e., the visual axis and point of regard, may be computed, by determining which photodetector 82 in the matrix of photodetectors 82 detected the highest intensity reflected light 91.

Another important advantage of the present invention is shown in FIG. 11 The outside surface of the transparent polymer 76 is given a coating 92 that reflects infrared light. It is intended that the reflective coating 92 be specifically reflective of light of the same frequency as that emitted by the light emitting diodes 80. Stray infrared light 94 from outside sources strikes the transparent polymer 76 and is reflected back by the reflective coating 92. Thus, the problem of the photodetectors 82 detecting stray light 94 from sources other than the light emitting diodes 80 is eliminated, helping to ensure that accurate eye position data is outputted.

Figure 12A:
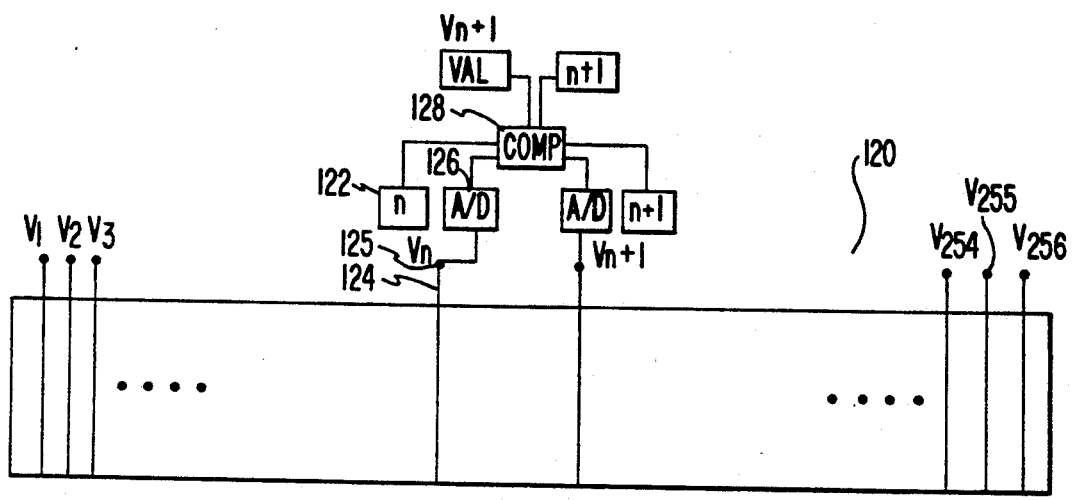
FIGS. 12A and 12B show one embodiment of the peripheral circuitry used in the invention to compute the visual axis, a pyramid cascade circuit.
Figure 12B:
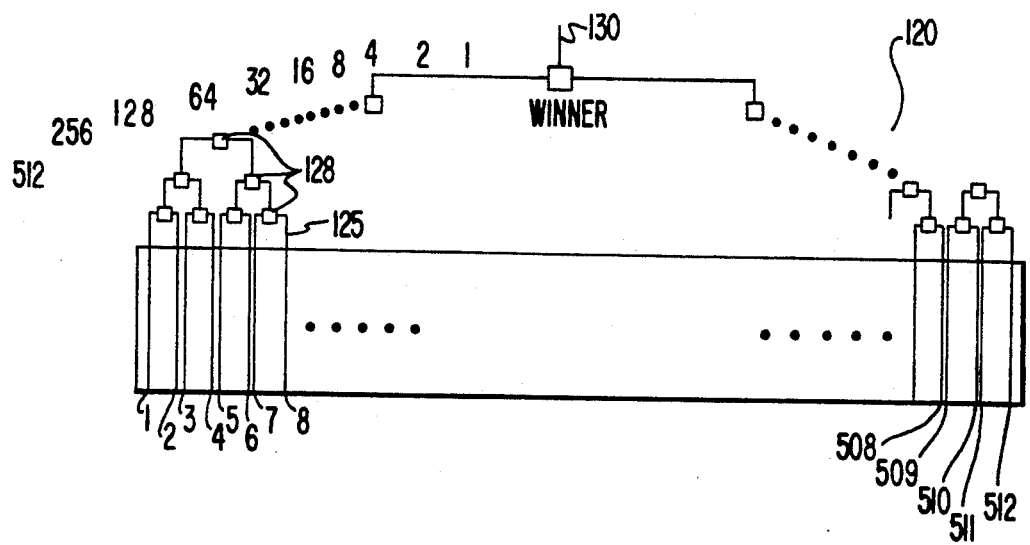

Turning now to FIGS. 12A and 12B, one of the methods of calculating the location of the row and column with the highest (or lowest) voltage value of any of the embodiments of the invention is shown. FIGS. 12A and 12B show a typical pyramid cascade circuit 120 known in the electrical engineering field. However, at this point in time it has not been implemented in eye tracking devices. As shown in FIG. 12A, a read only memory word 122 contains the hard-coded address of a specific row or column 124. Each voltage output 125 from that row or column is fed into an analog-to-digital converter 126, which converts the voltage output 125 into a numerical value. Between each pair of analog-to-digital converters 126 (corresponding to each pair of rows or columns) is a comparator 128, which compares the numerical values and selects the larger numerical value. This numerical value, and the hard-coded address of its corresponding row or column 124, is passed up to another level of comparators 128, as shown in FIG. 12B. This process is repeated until the row or column 124 with the highest numerical value is determined, which is the output 130 of the pyramid cascade circuit 120. This, of course, corresponds to the row or column 124 that has the greatest intensity fovea-reflected light impinging upon it. Devices of 10 the sort suitable for use in the pyramid cascade circuit described above are manufactured by Texas Instruments Corp.

One of the advantages of using a pyramid cascade circuit in an eye tracking device is the speed at which the location of the fovea-reflected light is determined. As an illustrative example, if a sample eye tracket has 512 columns of photodetectors (or, as will be discussed below, 512 columns of transparent resistive strips), there will be 256 comparators on the first level of comparators, 128 comparators on the second level, and so on until the ninth level, where a single comparator determines the location of the highest voltage. In general:

$$2^n = \text{number of columns}$$

where n=the number of comparator levels. The latency between the time a new signal appears at a column and the time it appears at the final comparator at the ninth level is n clock cycles. Thus, if the pyramid cascade circuit is clocked at 10 mega-hertz ($1 \times 10^{-7}$ seconds/cycle), and in the example n=9 (512 columns), the latency will be only 900 nanoseconds [$9 \times (1 \times 19^{-7}$ seconds)=$9 \times 10^{-7}$ seconds]. This is greater than one million samples per second, and is several orders of magnitude faster than the best eye tracker currently available.

It is intended that there be a pyramid cascade circuit to determine the row with the highest (or lowest) voltage value, and another pyramid cascade circuit to determine the column with the highest (or lowest) voltage value. The outputs of these two pyramid cascade circuits will be the address of the row with the highest (or lowest) voltage value and the address of the column with the highest (or lowest) voltage value. A radio frequency link will transmit these outputs to a remote computing station. The remote computing station will receive the addresses, and, from their intersection, determine the exact spot in the photodetector matrix (or resistive strip configuration, see below) that has the greatest intensity fovea-reflected light impinging on it.

Variations on the use of these pyramid cascade circuits are contemplated to be within the spirit of the invention and the examples given herein are intended to be merely illustrative, not limiting. For example, in order to reduce costs, the number of comparators in each circuit may be reduced (i.e., one comparator between every four rows instead of every two).

Figure 13A:
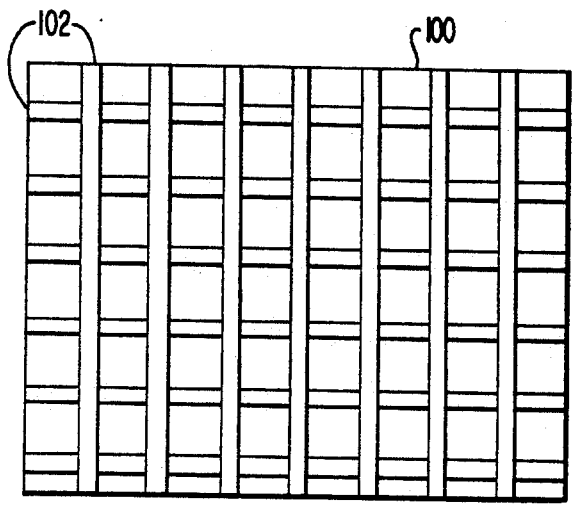
FIGS. 13A, 13B, and 13C show an alternative method of carrying out the invention, using a peripheral light source and an optical layer of resistive strips with reflective coatings.
Figure 13B:
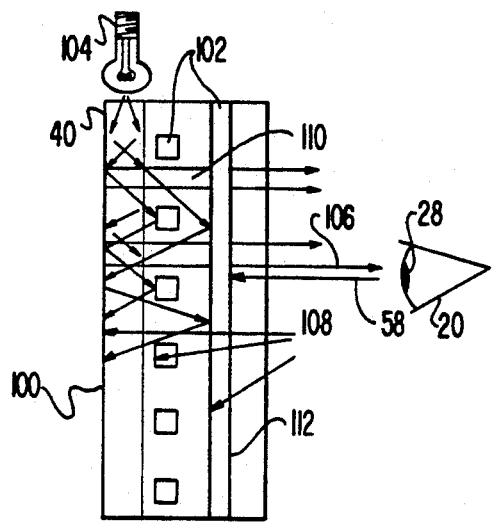
Figure 13C:
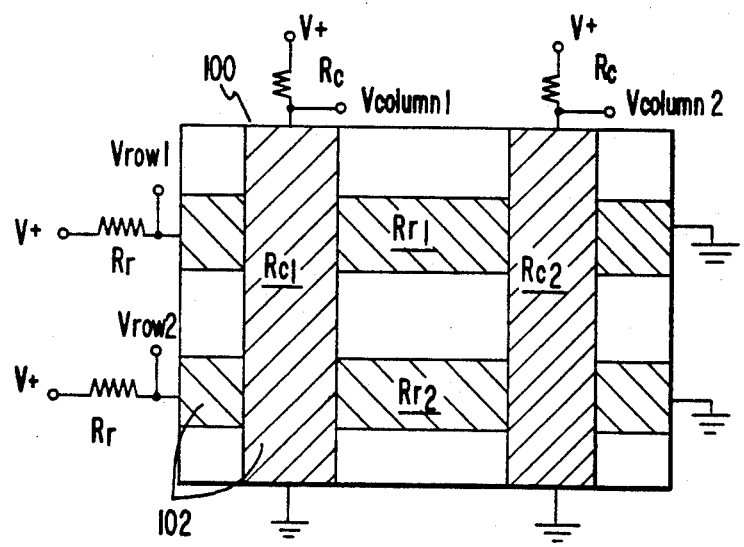

Variations of the embodiments described above are possible. For example, an alternate embodiment of the invention is shown in FIGS. 13A, 13B, and 13C. A transparent optical layer 100 is shown in FIG. 13A, overlaid with transparent resistive strips 102 in a row and column configuration. The transparent optical layer 100 and the overlaid transparent resistive strips 102 are curved in such a way so as to match the curvature of the eye (not shown). The transparent resistive strips 102 are fabricated so that their resistance changes with respect to the intensity of 10 light that impinges upon them. One type of implementation would be to "paint" a transparent photoresistive liquid in precise strips onto the optical layer 100. It is intended that the transparent optical layer 100 be any type of material conducive to bending or curving, such as glass, lexan, or polymer. It is 15 also required that the transparent optical layer 100 and the transparent resistive strips 102 appear transparent to visible light such that the user is able to look through them. The transparent optical layer 100 is mounted on a head apparel means (not shown) and extended around the head apparel means so as to be aligned with the optical axis of the eye (not shown). It is contemplated that the head apparel means be any type of head or facial apparel, such as helmets, goggles, glasses, or the like, and is not limited to those discussed here.

FIG. 13B is an exaggerated side view of the transparent optical layer 100, and shows its function. A peripheral light source 104 shines light 40 evenly across the transparent optical layer 100 and transparent resistive strips 102. Both the transparent optical layer 100 and the transparent resistive strips 102 are given a reflective coating 108 to their outer surfaces, the reflective coating 108 being specifically reflective to the frequency of the light 40 from the peripheral light source 104. Thus, light 40 from the peripheral light source 104 "bounces" off the reflective coatings 108 until it issues from the holes or spaces between the transparent resistive strips 102. The light 40 that escapes the transparent optical layer 100 impinges upon the surface of the eye 20, such that light 40 on the same path as the optical axis (not shown) passes through the pupil 28 and reflects off the fovea (not shown), as has been discussed previously. This fovea-reflected light 58 is directed back towards the transparent optical layer 100, where it impinges on the uncoated surface 112 of the transparent resistive strips 102. As a result, the resistance of the transparent resistive strips 102 changes, as described in FIG. 13C.

FIG. 13C shows an enlarged view of a section of the transparent optical layer 100. The transparent resistive strips 102 have variable resistance $R_{r1}$, $R_{c1}$, $R_{r2}$, and $R_{c2}$, which are a function of the intensity of the light incident to the surface of the transparent resistive strips 102. By examining the following formulas:

$$V_{column1} = \frac{R_{c1}(V+)}{R_{c1} + R_c} \quad V_{column2} = \frac{R_{c2}(V+)}{R_{c2} + R_c}$$

$$V_{row1} = \frac{R_{r1}(V+)}{R_{r1} + R_r} \quad V_{row2} = \frac{R_{r2}(V+)}{R_{r2} + R_r}$$

it is apparent that if the transparent resistive strips 102 increase in resistance with the intensity of the incident light, the greatest voltage value in the transparent optical layer 100 will be from the location of the transparent resistive strips 102 that have the highest intensity light impinging upon them (i.e., fovea-reflected light). Conversely, if the transparent resistive strips 102 decrease in resistance with the intensity of the incident light, the lowest voltage value in the transparent optical layer 100 will be from the location of the transparent resistive strips 102 that have the highest intensity light impinging upon them (i.e., fovea-reflected light).

FIG. 10 graphically depicts $V_{row}$ and $V_{column}$ as a function of the fovea reflection in the transparent optical layer. The row and column of the transparent resistive strips that have the highest intensity reflected light impinging upon them (i.e., the light reflected from the retina, and more specifically, the fovea) will output the highest (or lowest) voltage values. From this, the visual axis and point of regard may be computed. The second method of determining the highest (or lowest) voltage values is fully described below.

Figure 14A:
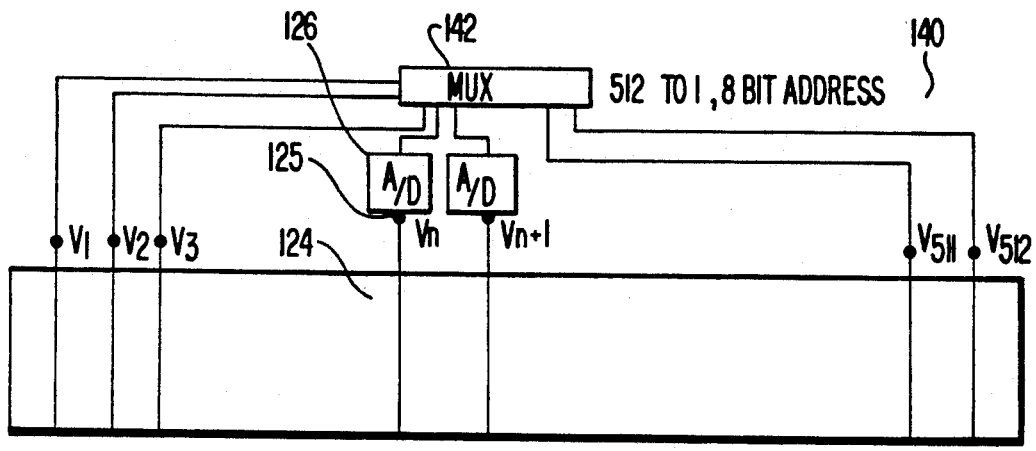
FIGS. 14A and 14B show another embodiment of the peripheral circuitry used in the invention to compute the visual axis, a microprocessor and digital multiplexor.
Figure 14B:
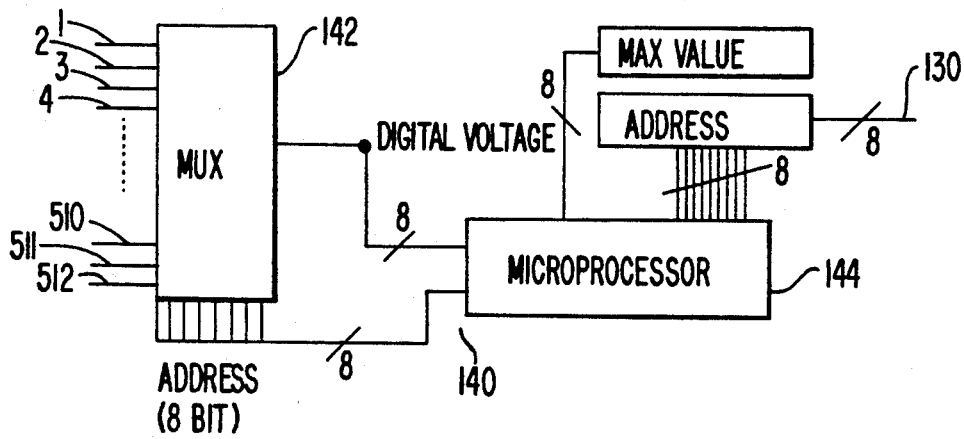

FIGS. 14A and 14B depict another method of calculating the location of the row and column with the highest (or lowest) voltage value of any of the embodiments of the invention. FIGS. 14A and 14B show a typical microprocessor circuit 140 known in the electrical engineering field. However, at this point in time it has not been implemented in eye tracking devices. In this method, each voltage output 125 from a row or column 124 is fed into an analog-to-digital converter 126, which converts the voltage output 125 into a numerical value. A digital counter (not shown) cycles through all the numerical addresses of each row or column 124 and inputs that address to a digital multiplexor 142. The digital multiplexor 142, which has access to all the rows or columns 124, selects the numerical value for the row or column 124 indicated by its address, and passes the numerical value stored at that address to the microprocessor 144, as shown in FIG. 14B. The microprocessor 144 sorts through all the numerical values, determines which is the greatest, and delivers the corresponding address to the output 130. This corresponds to the row or column that has the greatest intensity fovea-reflected light impinging upon it. Although this method is slower than the pyramid cascade circuit described above, it is still many times faster than any eye tracker currently available. Devices of the sort suitable for use in the microprocessor circuit described above are manufactured by Texas Instruments Corp.

It is intended that there be a microprocessor circuit to determine the row with the highest (or lowest) voltage value, and another microprocessor circuit to determine the column with the highest (or lowest) voltage value. The outputs of these two microprocessor circuits will be the address of the row with the highest (or lowest) voltage value and the address of the column with the highest (or lowest) voltage value. A radio frequency link will transmit these outputs to a remote computing station. The remote computing station will receive the addresses, and, from their intersection, determine the exact spot in the photodetector matrix (or resistive strip configuration) that has the greatest intensity fovea-reflected light impinging on it. Again, variations on the use of these microprocessor circuits will be obvious to one skilled in the art, and the examples given are intended to be merely illustrative, not limiting.

Another embodiment of the invention is shown in FIG. 15, that is, a lightweight, wireless eye and head tracker apparatus. This embodiment employs the preferred embodiment of the invention, the use of a matrix of light emitting diodes and a corresponding matrix of photodetectors embedded in a thin film of transparent polymer. The apparatus 150 has mounted on it a thin film of transparent polymer 76, with a matrix of light emitting diodes 80 and a corresponding matrix of photodetectors 82 embedded in the transparent polymer 76. The transparent polymer 76 is curved in such a way so as to match the curvature of the eye (not shown), and is extended around the inside surface 152 of the apparatus 150 so as to always be aligned with the optical axis of the eye. Thus, there is always a light emitting diode 80 and a corresponding photodetector 82 that is coincident with the optical axis of the eye, regardless of the position of the eye in the socket. A computing circuit 154 is mounted along with the transparent polymer 76 to calculate the position of the eye, as has been previously discussed. The computing circuit 154 can be either of the two types described above, the pyramid cascade circuit or the microprocessor circuit. A wireless head tracking device 156 is built in to the frame of the apparatus 150, in order to measure the reflective movement and amplitude of the head of the wearer (not shown). The head tracking device 156 can be any type of wireless navigation system currently on the market, such as a LORAN system. Receivers for these types of systems are manufactured by Motorola, Inc. Additionally, also mounted into the frame of the apparatus 150 is a wireless local area network device 158, which transmits the eye position and head position data to a remote computing station (not shown). The wireless local area network device 158 can be of any type currently on the market, such as the one manufactured by Motorola Inc.

FIG. 16 depicts another embodiment of the invention. When a person looks at an object 160, each eye 20 independently moves so as to place the object 160 within the view of the fovea 34. As a result, the object 160 falls in the line of each optical axis 36 of each eye 20. Two eye tracking devices 162 of the preferred embodiment of the invention, as discussed previously, are mounted onto an apparatus 150, one for each eye 20. When the eyes 20 focus on an object 160, the optical axes 36 of each eye 20 intersect in space at the point where the object 160 is located. By simple geometry, the distance d from the object 160 to the user may be determined, by computing the point of intersection of the two optical axes 36. It is envisioned that this dual eye tracking device be used in conjunction with CAD/CAM applications or other computer applications requiring an indication of a three dimensional point in space by a user.

Further variations on the embodiments described above are possible. For example, the transparent polymer or the transparent optical layer may be curved in order to be exactly calibrated to a specific user. In this embodiment, the precise curvature of a particular user's eye is measured, and the transparent polymer or transparent optical layer is then curved to exactly match the measured eye. In this way, even the most minute discrepancies of a particular user's eye will be accounted for, yielding extremely accurate eye position information.

The embodiments described above provide a number of significant advantages. The ability to curve the transparent polymer or the transparent optical layer results in the light detecting devices always being co-incident with the optical axis of the eye, so as to yield highly accurate, linear eye position results. Another important advantage of this invention is the use of circuitry to determine the location of fovea-reflected light, such as a pyramid cascade circuit or a microprocessor circuit, that computes the visual axis and point of regard at speeds faster than any previously disclosed eye tracker. Yet another advantage is the use of a mild reflector on the outside surface of the transparent polymer or transparent optical layer in order to keep the amount of external light that impinges on the eye (i.e., light noise) at a minimum, thus increasing the accuracy of the eye position results. Implementing the devices in thin film results in a lightweight, mobile one-piece eye tracker that eliminates the need for cumbersome mirrors and video cameras.

Of course, it should be understood that a wide range of changes and modifications can be made to the embodiments described above. It is therefore intended that the foregoing detailed description be regarded as illustrative rather than limiting, and that it be understood that it is the following claims, including all equivalents, which are intended to define the scope of this invention.

I claim:

1. An eye tracking device comprising a plurality of light emission means for transmitting near infrared collimated light in the direction of the human eye, said near infrared collimated light disposed for transmission through the pupil and reflection off the retina in such a way that the brightest reflected near infrared collimated light occurs from the fovea, a plurality of light detection means, corresponding in location to said light emission means such that for every light emission means there is at least one corresponding light detection means, for detection of said reflected near infrared collimated light, said light detection means being positioned in such a way as to be coincident with the optical axis of the eye, and computation means for computing the visual axis and point of regard from the fovea reflected light.

2. The eye tracking device of claim 1, whereby the wavelength of the near infrared collimated light is between about 675 to about 740 nm.

3. The eye tracking device of claim 2, whereby the wavelength of the near infrared collimated light is between about 700 to about 740 nm.

4. The eye tracking device of claim 3, whereby the wavelength of the near infrared collimated light is between about 720 to about 740 nm 5. The eye tracking device of claim 1 whereby the light emission means and the light detection means are embedded in a curved transparent thin film.

6. The eye tracking device of claim 5 whereby the curvature of the transparent thin film conforms to the curvature of the eye.

7. The eye tracking device of claim 6 whereby the curved transparent thin film is mounted on head apparel means and extended around said head apparel means so as to correspond to the optical axis of the eye, such that the embedded light emission means and the embedded light detection means are always coincident with said optical axis of the eye.

8. The eye tracking device of claim 7 whereby the outside surface of the head apparel means is equipped with a mild reflector on said outside surface, said mild reflector being reflective or external light sources of the same frequency as the near infrared collimated light emitted by the light emission means.

9. The eye tracking device of claim 6, wherein said device is calibrated to any individual user by measuring the curvature of said individual's eye and curving the transparent thin film of polymer so as to parallel said eye curvature.

10. The eye tracking device of claim 1 whereby the plurality of light emission means is a matrix of light emitting diodes.

11. The eye tracking device of claim 1 whereby the plurality of light detection means is a matrix of photodetectors.

12. The eye tracking device of claim wherein said computation means comprises a pyramid cascade circuit comprising a plurality of read only memory words which contain the hard coded address for each row and column of the light detection means, a plurality of analog to digital converters for converting the voltage output of each row and column of said light detection means to a numerical value, and a plurality of comparators between each pair of said rows and columns for comparing said numerical values and selecting the larger of the two, passing said larger numerical value and said address up to the next level of comparators, until the address with the largest numerical value is outputted.

13. The eye tracking device of claim 12 whereby two pyramid cascade circuits are utilized, one for the rows of light detection means and one for the columns of light detection means.

14. The eye tracking device of claim 1 whereby the light emission means is a matrix of light emitting diodes, the light detection means is a matrix of photodetectors, and said computation means is a pyramid cascade circuit.

15. The eye tracking device of claim 1 wherein said computation means comprises a microprocessor, said microprocessor comprising a plurality of analog to digital converters for converting the voltage output of each row and column of the light detection means to a numerical value, and a digital multiplexor for selecting the numerical value that corresponds to its address in each row and column of said light detection means, said microprocessor being programmed in such a way that it sorts through all of said rows and columns, determines which has the highest numerical value, and outputs the address of said row and column with said highest numerical value.

16. The eye tracking device of claim 15 whereby two microprocessor circuits are utilized, one for the rows of light detection means and one for the columns of light detection means.

* * * * *

UNITED STATES PATENT AND TRADEMARK OFFICE
CERTIFICATE OF CORRECTION

PATENT NO. : 5,270,748
DATED : December 14, 1993
INVENTOR(S) : Warren J. Katz

It is certified that error appears in the above-indentified patent and that said Letters Patent is hereby corrected as shown below:

Col. 1, line 42, delete "10".

Col. 2, line 23, delete "or rne" and insert --of the--.

Col. 5, line 37, delete "focussing" and insert --focusing--

Col. 8, lines 42-43, delete "focussed" and insert --focused--.

Col. 9, line 15, after "evident" insert a period.

Col. 11, line 61, delete "10".

Col. 11, line 67, delete "tracket" and insert --tracker--.

UNITED STATES PATENT AND TRADEMARK OFFICE
CERTIFICATE OF CORRECTION

PATENT NO. : 5,270,748
DATED : December 14, 1993
INVENTOR(S) : Warren J. Katz

It is certified that error appears in the above-indentified patent and that said Letters Patent is hereby corrected as shown below:

Col. 12, line 52, delete "10".

Col. 12, line 58, delete "15".

Col. 13, line 47, delete "$V_{row\ and\ Vcolumn}$" and insert --$V_{row}$ and $V_{column}$--.

Col. 16, Claim 12, line 48, after "claim" insert --1--.

Signed and Sealed this

Tenth Day of January, 1995

Attest:

BRUCE LEHMAN

*Attesting Officer*     *Commissioner of Patents and Trademarks*